United States Patent
Kim et al.

(10) Patent No.: US 11,614,321 B2
(45) Date of Patent: Mar. 28, 2023

(54) METHOD AND APPARATUS FOR MEASURING TEAR FILM THICKNESS USING OPTICAL INTERFERENCE

(71) Applicant: TOPCON CORPORATION, Tokyo (JP)

(72) Inventors: Jongsik Kim, Fort Lee, NJ (US); Bin Cao, Wayne, NJ (US); Song Mei, Franklin Park, NJ (US); Kinpui Chan, Ridgewood, NJ (US); Zhenguo Wang, Ridgewood, NJ (US); Zaixing Mao, Edgewater, NJ (US)

(73) Assignee: TOPCON CORPORATION, Tokyo (JP)

( * ) Notice: Subject to any disclaimer, the term of this patent is extended or adjusted under 35 U.S.C. 154(b) by 108 days.

(21) Appl. No.: 16/829,673

(22) Filed: Mar. 25, 2020

(65) Prior Publication Data
US 2020/0309510 A1  Oct. 1, 2020

Related U.S. Application Data

(60) Provisional application No. 62/826,495, filed on Mar. 29, 2019.

(51) Int. Cl.
| | | |
|---|---|---|
| G01C 1/04 | (2006.01) | |
| A61B 3/10 | (2006.01) | |
| A61B 3/113 | (2006.01) | |
| A61B 3/14 | (2006.01) | |
| A61B 3/12 | (2006.01) | |
| G01B 11/06 | (2006.01) | |

(52) U.S. Cl.
CPC .......... *G01B 11/0675* (2013.01); *A61B 3/101* (2013.01); *A61B 3/113* (2013.01); *A61B 3/14* (2013.01)

(58) Field of Classification Search
CPC ......... A61B 3/14; A61B 3/103; A61B 3/1225; A61B 3/024; A61B 3/032; A61B 3/18; A61B 3/1015; A61B 3/107; A61B 3/152; A61B 5/14542; A61B 5/4266; A61B 5/0059; A61B 6/032; G02C 7/02
USPC ............... 351/106, 200, 206, 205, 209, 210, 351/221–223, 245–246, 212, 208, 247
See application file for complete search history.

(56) References Cited

U.S. PATENT DOCUMENTS

| | | | |
|---|---|---|---|
| 2007/0046953 A1 | 3/2007 | De Groot et al. | |
| 2007/0213792 A1* | 9/2007 | Yaroslavsky | A61N 5/0613 607/100 |
| 2008/0273171 A1* | 11/2008 | Huth | A61B 3/101 356/504 |

(Continued)

OTHER PUBLICATIONS

Hwang et al., "Image-based quantitative analysis of tear film lipid layer thickness for meibomian gland evaluation", BioMedical Engineering OnLine, 2017, 16:135, pp. 1-15.

(Continued)

*Primary Examiner* — Dawayne Pinkney
(74) *Attorney, Agent, or Firm* — Pearne & Gordon LLP

(57) ABSTRACT

An interferometric method of identifying the thickness of an object that is too thin to be resolved by a Fourier transform of the interference signal includes applying a harmonic frequency modulation to an envelope of the interference signal. Where the object is a tear film, this method may be utilized to determine a thickness of the lipid layer of the tear film.

21 Claims, 7 Drawing Sheets

(56) References Cited

U.S. PATENT DOCUMENTS

| | | | |
|---|---|---|---|
| 2013/0208968 A1* | 8/2013 | Hanebuchi | A61B 5/0066 382/131 |
| 2016/0338585 A1* | 11/2016 | Arieli | A61B 3/1005 |
| 2017/0188815 A1 | 7/2017 | Huang et al. | |
| 2018/0042472 A1 | 2/2018 | Grenon et al. | |
| 2019/0017804 A1 | 1/2019 | Arieli et al. | |

OTHER PUBLICATIONS

Bai et al., "In vivo thickness measurement of the lipid layer and the overall tear film by interferometry", Optics Letters, vol. 44, No. 10, May 15, 2019, pp. 2410-2413.

Jansonius et al., "Influence of coherence length, signal-to-noise ratio, log transform, and low-pass filtering on layer thickness assessment with OCT in the retina", Biomedical Optics Express, vol. 7, No. 11, Nov. 1, 2016, http://dx.doi.org/10.1364/BOE.7.004490, pp. 4490-4500.

Groot, "Interference Microscopy for Surface Structure Analysis, Handbook of Optical Metrology: Principles and Applications", Edition: Second Edition, Chapter: 31, Publisher: CRC Press, Apr. 20, 2020, pp. 791-828.

Zhang et al., "Methods and algorithms for optical coherence tomography-based angiography: a review and comparison", Journal of Biomedical Optics, vol. 20, No. 10, Oct. 2015, pp. 100901-100901-13.

Wu et al., "Multilayer thin-film inspection through measurements of reflection coefficients", Optics Letters, vol. 36, No. 16, Aug. 15, 2011, pp. 3269-3271.

Kim et al., "Thickness Measurement of a Transparent Thin Film Using Phase Change in White-Light Phase-Shift Interferometry", Current Optics and Photonics, vol. 1, No. 5, Oct. 2017, pp. 505-513.

Extended European Search Report for European Application No. 20166633.6 dated Aug. 5, 2020.

* cited by examiner

METHOD AND APPARATUS FOR MEASURING TEAR FILM THICKNESS USING OPTICAL INTERFERENCE

CROSS REFERENCE TO RELATED APPLICATIONS

This application claims priority to U.S. Provisional Application No. 62/826,495, filed on Mar. 29, 2019, entitled "METHOD AND APPARATUS FOR MEASURING TEAR FILM THICKNESS USING OPTICAL INTERFERENCE", the entirety of which is incorporated herein by reference.

BACKGROUND OF THE INVENTION

Dry eye has become one of the most common causes for ophthalmological doctor visits. Dry eye is a multifactorial disease of the ocular surface that is related to the tear film, in which the eye does not have enough tears to adequately lubricate and nourish the eye. One method to diagnosing dry eye is to assess the quantity of tears by measuring the thickness of the tear film. As illustrated in FIG. 1, the tear film 100 comprises an outer lipid layer 102, a middle aqueous layer 104, and an inner mucin (mucus) layer 106. The lipid layer 102 is about 50 nm thick, the aqueous layer 104 is about 950 nm thick, and the mucin layer 106 is about 500 nm thick. The cornea is adjacent the tear film inside the mucin layer.

Currently, few technologies exist for imaging and analyzing the layers of the tear film (e.g., determining thicknesses of the tear film itself, and the layers therein) to objectively assist dry eye diagnosis, and diagnosis of other conditions related to the tear film. When using interferometric techniques, interference between reflections of light from the tear film layers may appear as a form of oscillations in the reflectance spectra (interference signal). To recover the depth profile from the interference signal, a Fourier transform is applied to the interference signal. However, the lipid layer may be too thin to be resolved by a Fourier transform used to reconstruct a depth profile from an interference signal. This is because when the detected interference signal length (or observation duration) is relatively short compared to the interference period, the interference signal of the lipid layer in the frequency domain is too close to the DC term, and thus cannot be differentiated from the DC term or noise. This is seen in FIG. 2, which illustrates an example depth profile of an interferogram signal. The portion of the signal corresponding to the combined thickness of the lipid and aqueous layers is clearly identifiable as the peak at about 1 μm; however, the portion of the signal corresponding to the lipid layer is not identifiable in the depth profile—that is, no separate peak is visible at the lipid layer depth of about 50 nm. This makes it difficult to resolve the lipid layer thickness from the resulting depth profile using an analysis method such as a Fourier transform directly.

Accordingly, some have attempted to estimate the lipid layer thickness with techniques such as curve fitting and comparisons to pre-calculated tables determined from various simulations and calibrations. However, these existing methods (e.g., curve fitting and pre-calculated tables) may be subject to certain limitations to consistently provide accurate lipid layer thicknesses. For example, curve fitting methods sometimes do not converge to a solution (a thickness measurement). And pre-calculated tables may be subject to predetermined measurement resolution.

BRIEF SUMMARY OF THE INVENTION

According to a first example, an interferometric method comprises: obtaining an interference signal from an object having a first layer and a second layer, the interference signal being generated by an interferometric imaging system; after obtaining the interference signal: determining a first interference signal component of the interference signal that corresponds to a depth of the first layer; and determining a second interference signal component of the interference signal that corresponds to a depth of the second layer; and after determining the first interference signal component: determining a thickness of the first layer based on the first interference signal component; and determining a thickness of the second layer based on the thickness of the first layer and the second interference signal component.

In various embodiments of the above example, the object further has a third layer, the second layer being between the first and third layers, the method further comprises: after obtaining the interference signal: determining a third interference signal component of the interference signal that corresponds to a depth of the third layer; and after determining the first, second, and third interference signal components: determining a thickness of the third layer based on the second interference signal component and the third interference signal component; determining the first interference signal component comprises: computing an envelope of the interference signal; iteratively applying a harmonic frequency modulation to the envelope a predetermined number of times, thereby generating a time domain modulated signal; performing a Fourier transform of the time domain modulated signal, thereby generating a frequency domain modulated signal; and identifying a frequency of the frequency domain modulated signal having a greatest intensity, and then converting the identified frequency to a depth, the depth corresponding to the depth of the first layer, or converting the frequency domain modulated signal to a depth profile, and then identifying a depth of the depth profile having a greatest intensity, the depth having the greatest intensity corresponding to the depth of the first layer; the method further comprises: compensating the time domain modulated signal for attenuation caused by the harmonic frequency modulation; the thickness of the first layer is equal to the depth of the first layer; the method further comprises: analyzing or estimating optical and/or fluid properties of the object based on the time domain modulated signal and/or the frequency domain modulated signal; determining the second interference signal component comprises: performing a Fourier transform of the interference signal, thereby generating a frequency domain interference signal; and identifying a frequency of the frequency domain interference signal having a greatest intensity, and then converting the identified frequency to a depth, the depth corresponding to the depth of the second layer, or converting the frequency domain interference signal to a depth profile, and then identifying a depth of the depth profile having a greatest intensity, the depth having the greatest intensity corresponding to the depth of the second layer; the thickness of the second layer is equal to the difference between the depth of the first layer and the depth of the second layer; the method further comprises: preprocessing the interference signal prior to determining the first and second interference signal components; the preprocessing comprises suppressing a DC term of the interference signal; the object is a tear film of the eye; the first layer is a lipid layer, and the second layer is an aqueous layer or a mucin layer; and/or the first layer is too thin to be resolved by a Fourier transform of the interference signal or of the interference signal having a DC term suppressed.

According to a second example, a method of determining a thickness of an object comprises: obtaining an interference signal from the object; computing an envelope of the interference signal; iteratively applying a harmonic frequency modulation to the envelope a predetermined number of times, thereby generating a time domain modulated signal; performing a Fourier transform of the modulated signal, thereby generating a frequency domain modulated signal; and identifying a frequency of the frequency domain modulated signal having a greatest intensity, and then converting the identified frequency to a depth, the depth corresponding to the thickness of the object, or converting the frequency domain modulated signal to a depth profile, and then identifying a depth of the depth profile having a greatest intensity, the depth having the greatest intensity corresponding to the thickness of the object.

In various examples of the second example, the method further comprises: compensating the time domain modulated signal for attenuation caused by the harmonic frequency modulation; the method further comprises: preprocessing the interference signal prior to computing the envelope of the interference signal; the preprocessing comprises suppressing a DC term of the interference signal; the object is a tear film of the eye, and the thickness is of a lipid layer of the tear film; the first layer is too thin to be resolved by a Fourier transform of the interference signal or of the interference signal having a DC term suppressed; and/or the method further comprises: analyzing or estimating optical and/or fluid properties of the object based on the time domain modulated signal and/or the frequency domain modulated signal.

DETAILED DESCRIPTION OF THE INVENTION

Figure 1:
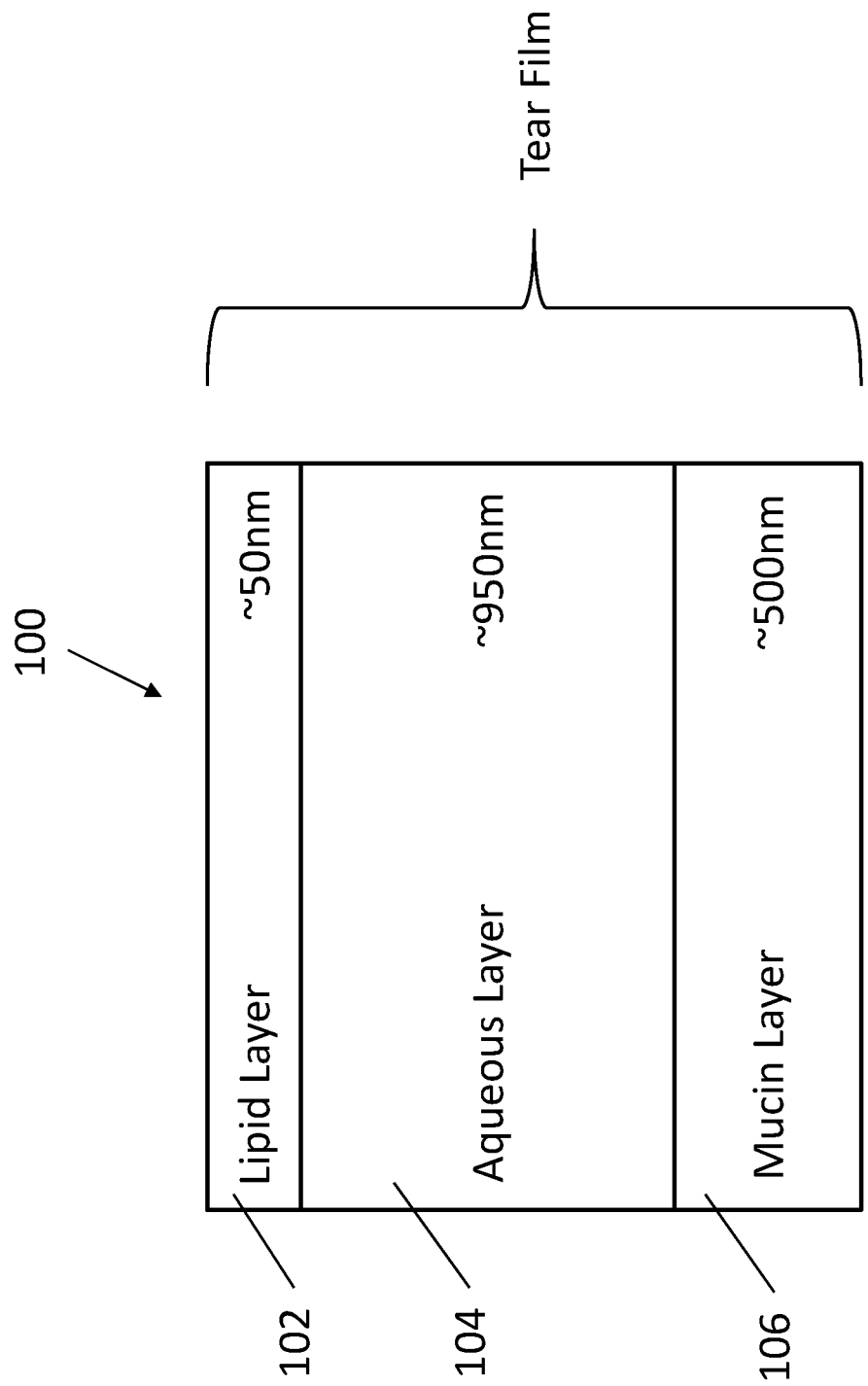
FIG. 1 schematically illustrates the tear film.
Figure 2:
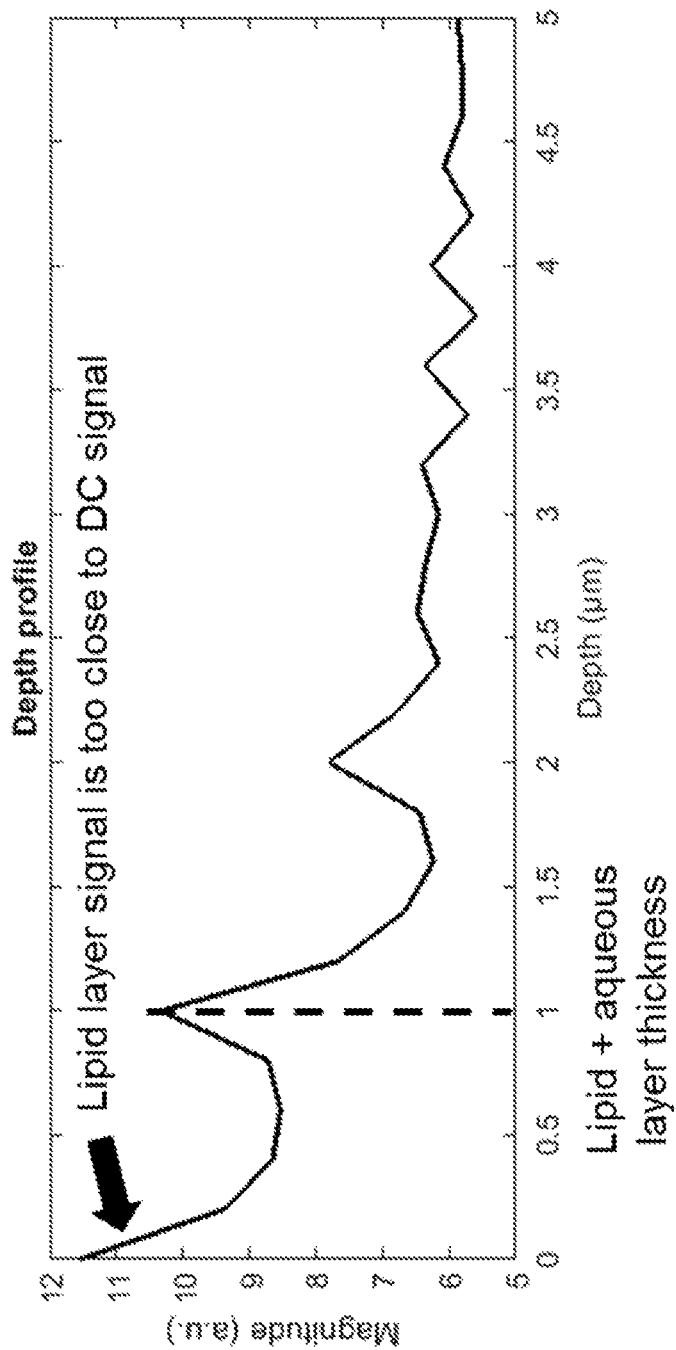
FIG. 2 illustrates an example depth profile of an interferogram signal.

In view of the above, the present disclosure relates to the determination of tear film layer thicknesses that overcome the above-noted limitations. When performing thickness measurements with interferometric techniques (e.g., via low coherence tomography or an optical coherence tomography system), interference signals correspond to different wavelengths of incident light detected from each location of the tear film being measured. These interference signals are defined below relative to a lipid layer thickness component (L), an aqueous layer thickness component (A), and a mucin layer thickness component (M):

OpticalInterference #1=$L$

OpticalInterference #2=$L+A$

OpticalInterference #3=$L+A+M$ where OpticalInterference #1 is an interference signal from the lipid/aqueous layer interface (corresponding to a lipid layer thickness/depth), OpticalInterference #2 is an interference signal from the aqueous/mucin layer interface (corresponding to a thickness/depth of the lipid layer plus the aqueous layer depth), and OpticalInterference #3 is an interference signal from the base of the mucin layer (corresponding to a thickness/depth of the lipid layer plus the aqueous layer plus the mucin layer depth). In other words, the lipid layer thickness is equal to the depth corresponding to the frequency of OpticalInterference #1, the aqueous layer thickness is equal to the difference between the depths corresponding to the frequencies of OpticalInterference #2 and OpticalInterference #1, and the mucin layer thickness is equal to the difference between the depths corresponding to the frequencies of OpticalInterference #3 and OpticalInterference #2:

$L$=OpticalInterference #1

$A$=OpticalInterference #2−$L$=OpticalInterference #2−OpticalInterference #1

$M$=OpticalInterference #3−$(L+A)$=OpticalInterference #3−OpticalInterference #2

Both L+A and L+A+M thicknesses can be resolved and calculated by taking Fourier transforms of OpticalInterference #2 and OpticalInterference #3 because the thicknesses of both the aqueous and the mucin layers are relatively thick enough (or higher in frequency so that they can be resolved by taking the Fourier transform) to be seen by such an analysis of the interference signal. However, as noted above, the lipid layer is too thin to have its thickness resolved this way. Further, because OpticalInterference #2 includes the lipid layer thickness component, the actual thicknesses of the aqueous layer cannot be fully determined. While OpticalInterference #3 also includes the lipid layer thickness component, the mucin layer thickness can be determined without knowing the lipid layer thickness by subtraction of the L+A (which is known from OpticalInterference #2) depth from OpticalInterference #3, as shown above.

The method of the present disclosure is capable of determining the thicknesses of each of the lipid, aqueous, and mucin layers. One example of this method is illustrated in the flow charts of FIGS. 3-6. Briefly, the depths corresponding to OpticalInterference #2 and OpticalInterference #3 are resolved by taking the Fourier transform; and in parallel, the lipid layer thickness (OpticalInterference #1) is determined by a harmonic frequency modulation method. Lastly, the aqueous layer and mucin layer thicknesses are calculated from the determined lipid layer thickness.

Figure 3:
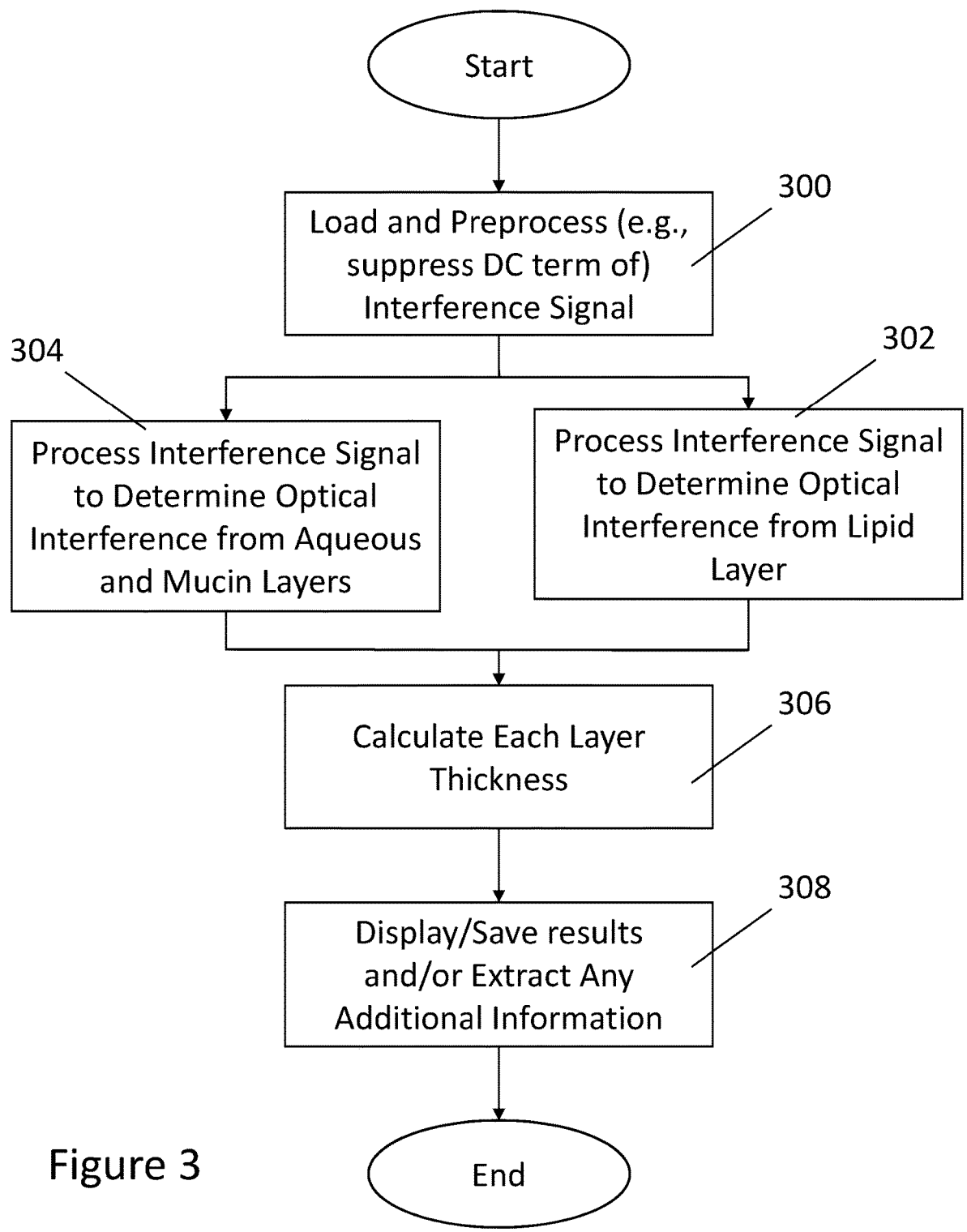
FIG. 3 illustrates an example method of the present disclosure for determining each of the lipid, aqueous, and mucin layer thicknesses.
Figure 6:
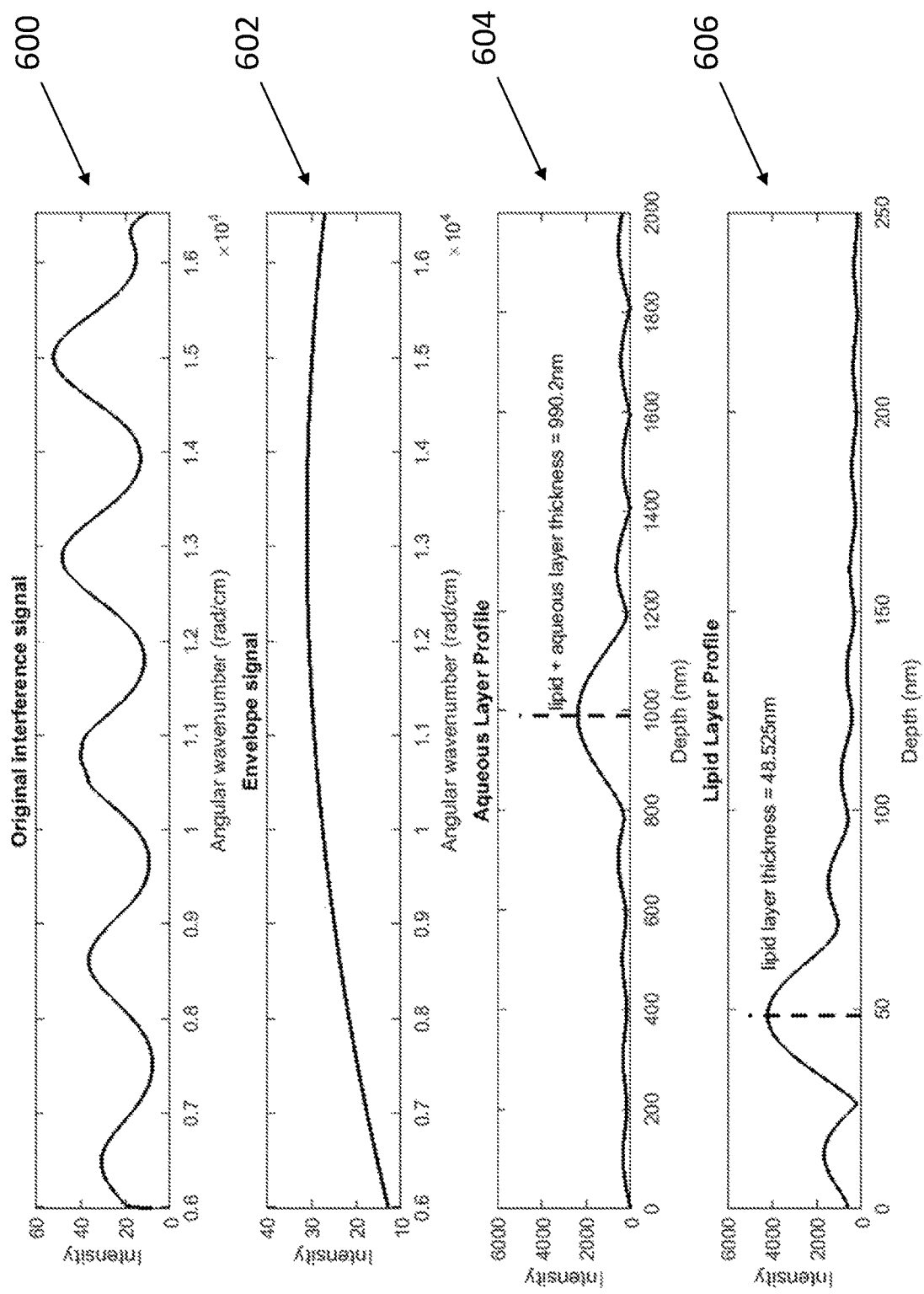
FIG. 6 illustrates example signals determined in the example methods of FIGS. 3-5.

More particularly, as shown in FIG. 3, the method begins by loading and preprocessing an interference signal 300 (herein, 'interference signal' is used herein to refer to both pre-processed and non-pre-processed interference signals). An example of an interference signal 600 is illustrated in FIG. 6. After obtaining and loading the interference signal, the interference signal is preprocessed, for example, by suppressing of a DC term in the interference signal. The DC term of the interference signal represents a low frequency signal close to a DC offset level (at zero frequency). Suppressing the DC term may thus be accomplished by applying a filter (e.g., an analog and/or digital low pass filter, median filter, mean filter, band pass filter, moving average filter, or the like). In other embodiments, the DC term can be suppressed by taking the first derivative of the detected interference signal. Of course other similar signal processing techniques may be used to remove the corresponding frequencies, subtraction of the DC level, or the like, and to remove and/or suppress other noises. For example, the background noise as a function of wavenumber, as measured from a system calibration procedure or the like, can simply be subtracted from a loaded or otherwise acquired optical interference signal 600 in order to remove the background noise. It is further noted that other types of noise can be suppressed before, after, or during a background noise suppression procedure. Each type of noise suppression may be realized by various types of analog and/or digital filters such as mean filter, low pass filter, band pass filter, median filter, or the like, and/or via software processing.

Following preprocessing 300, the measurement of a depth corresponding to OpticalInterference #1 (as described above) 302 occurs in parallel with a depth measurement of OpticalInterference #2 and OpticalInterference #3 (as also described above) 304.

Figure 4:
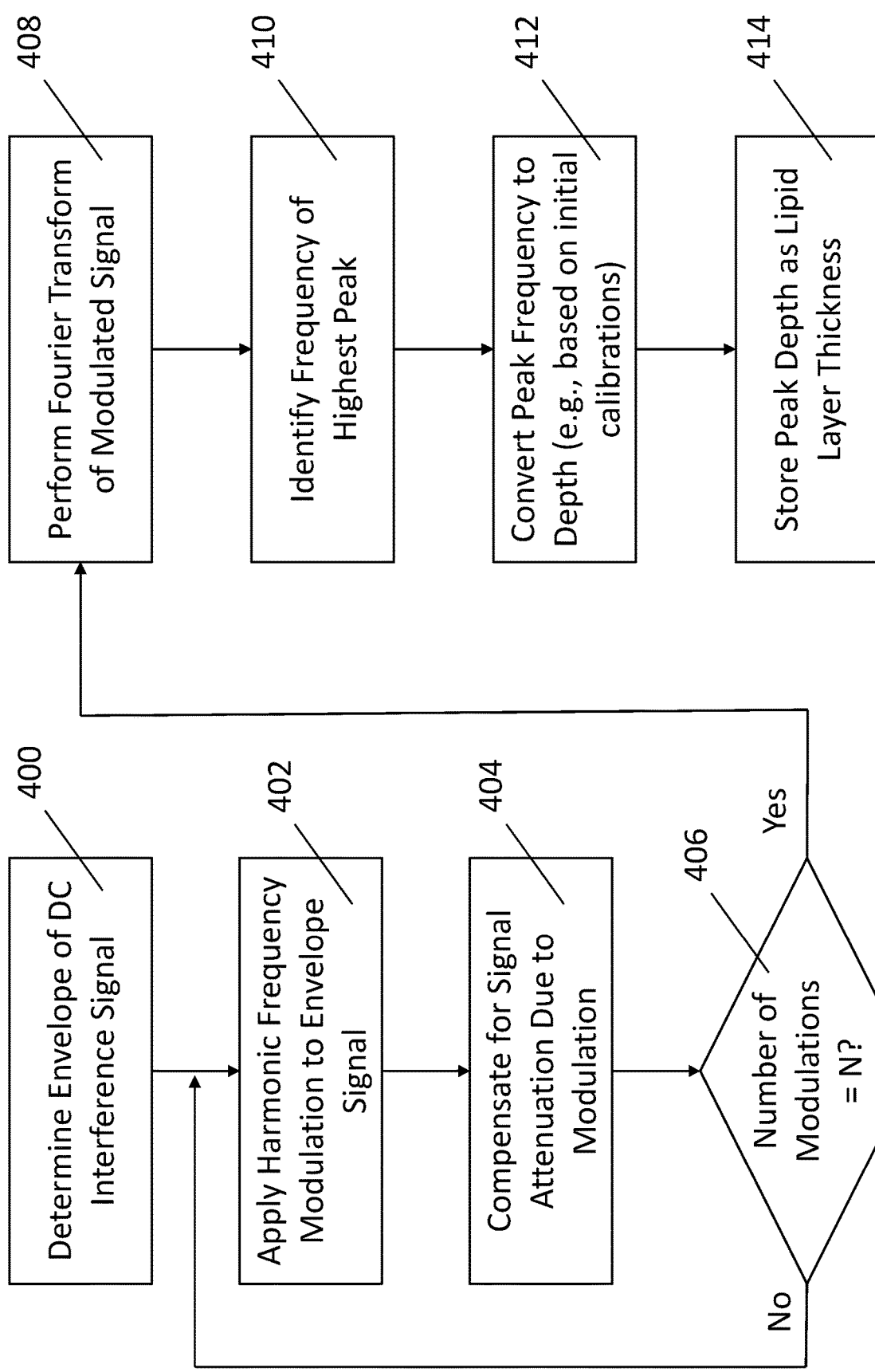
FIG. 4 illustrates an example method of the present disclosure for determining lipid layer thickness.

An example method for measuring OpticalInterference #1 is shown in FIG. 4. Therein, the envelope of the interference signal (e.g., the interference signal with a suppressed DC term) is first determined 400. An example resulting envelope signal 602 is illustrated in FIG. 6 (showing an envelope of the interference signal 600 of FIG. 6). In some embodiments, a polynomial curve may be fit to the detected interference signal 600 to obtain the interference signal portion OpticalInterference #1. The resulting envelope signal may be modeled as an arbitrary signal (e.g., a sine or cosine function).

The envelope signal is then modulated according to a harmonic frequency (harmonic frequency modulation, described in more detail below) 402, and the resulting signal is compensated for 404 due to attenuation caused by the modulation 402. This modulation and compensation is repeated (N times) as an iterative process. The number of modulations (N) may be predetermined according to a desired result, for example, at least until the DC term can be differentiated from modulated signal or the signal-to-noise ratio reaches a desired or maximum level. The result or the specific number of modulations may be selected by a user, or may be automated. In some embodiments, three iterations may be preferred. This harmonic modulation 402, 404 allows the lipid layer to be resolved by a later Fourier transform 408. It is noted that in some embodiments the compensation for attenuation 404 may be performed after the N modulations are applied.

Harmonic frequency modulation is a special case of a ring modulation signal-processing function, which has typically been reserved for music synthesis and sound effects. Ring modulation is performed by multiplying two signals, one of which is typically a sine wave or another simple waveform (a modulating signal), and the other of which is the signal being modulated (an envelope signal). With harmonic frequency modulation, the two signals being multiplied preferably have the same frequency but may have different phases and/or amplitudes (e.g., the signals may be 90° out of phase.) This concept of the harmonic frequency modulation is illustrated in the following example equations, with the signals being multiplied on the left and the resulting modulated signal on the right:

$$A\sin(\alpha) \times B\cos(\alpha) = \frac{AB}{2}\sin(2\alpha)$$

$$A\cos(\alpha) \times B\cos(\alpha) = \frac{AB}{2}[\cos(2\alpha) + 1]$$

$$A\sin(\alpha) \times B\sin(\alpha) = \frac{AB}{2}[1 - \cos(2\alpha)]$$

As can be seen from these examples, if the multiplied signals (represented as sine and cosine functions) are identical in frequency, then the resulting modulated signal has twice the frequency of the original signals. It thus follows that the resulting frequency shift is equal to $2^N$, where N represents the number of repeated modulations, without limitation. If the frequencies of the two signals are different, a subharmonic frequency shift less than $2^N$ could still be observed. While it is noted that the above equations are based on the product identities of the trigonometric functions, other trigonometric identities (or properties) can also be considered to achieve similar outcome of the harmonic frequency modulation such as product-to-sum identities, angle-sum and -difference identities, double-angle identities, sum identities, etc.

In particular, as can be seen in the above example equations, the amplitude of the harmonic frequency modulated signal is attenuated by half from the original input envelope signal for each iteration of the modulation. Thus if the rate of signal attenuation per modulation is significant, the amount of attenuation per modulation can be compensated by multiplying a constant value to the modulated signal. Alternatively, the attenuation can be compensated for at the same time as modulation, for example, by using a modulating signal having twice the amplitude (or like factor) of the envelope signal. However, in some embodiments the amount of signal attenuation may not be significant enough to justify compensation when the amplitude of the input envelope signal is relatively high. In addition to the modulating signal manipulating the frequency and amplitude of the modulated signal as discussed above, the phase of the modulated signal may also be manipulated by altering the phase of the modulation signal relative to the envelope signal.

As noted above, the envelope signal can be modeled as a sine or cosine function. The harmonic modulating signal to be multiplied with the envelope signal can be formed by any method. For example, a Hilbert transform or first derivation technique can be employed to generate the harmonic modulating signal having the same frequency but, for example, 90° out of phase relative to the envelope signal. The result of multiplication of the envelope signal with the harmonic modulating signal is a harmonic frequency modulated envelope signal. As also noted above, the amplitude of the harmonic frequency modulated envelope signal may be compensated and/or be modulated again by multiplication with another harmonic modulating signal. The compensation may be applied by multiplying the resulting harmonic frequency modulated envelope signal by a scaling factor determined by a user or based on predetermined optimum values. The scaling factor may be selected, for example, to maintain a desired signal-to-noise ratio.

Returning to FIG. 4, after the envelope signal is modulated and attenuation due to modulation is compensated for, a Fourier transform is performed 408 on the harmonic frequency modulated envelope signal in the time domain. The Fourier transform produces a power spectrum of the modulated envelope signal in the frequency domain (or spatial domain in optical coherence tomography). The highest peak (the greatest frequency component in the modulated signal) is then identified (e.g., by peak detection methods) 410 and the corresponding frequency is converted into a depth 412. The conversion may be based on an initial calibration of the imaging system that obtained the interference signal. For example, a tear film mimicking calibration sample with comparable thickness(es) and refractive index of tear film (e.g., 1.337) can be used to calibrate the system by to associate thicknesses of the calibration sample and corresponding frequencies. The identified depth corresponds to OpticalInterference #1, which is equal to the lipid layer thickness (L). A depth profile (where all frequencies have been converted to depth) of the modulated envelope signal in the frequency domain 606 is shown in FIG. 6. In the example of FIG. 6, the input interference signal was modulated three times, and amplified by a fixed scale factor after each modulation to preserve the original signal-to-noise ratio. As seen in FIG. 6, the depth corresponding to the identified greatest peak (the highest signal intensity) of lipid layer depth profile 606 is 48.5225 nm. Alternatively, the frequency domain modulated signal may be first converted to the depth profile 606, and then the greatest peak identified from the depth profile rather than the frequency domain modulated signal. The identified depth can then be stored 414 for later analysis.

Figure 5:
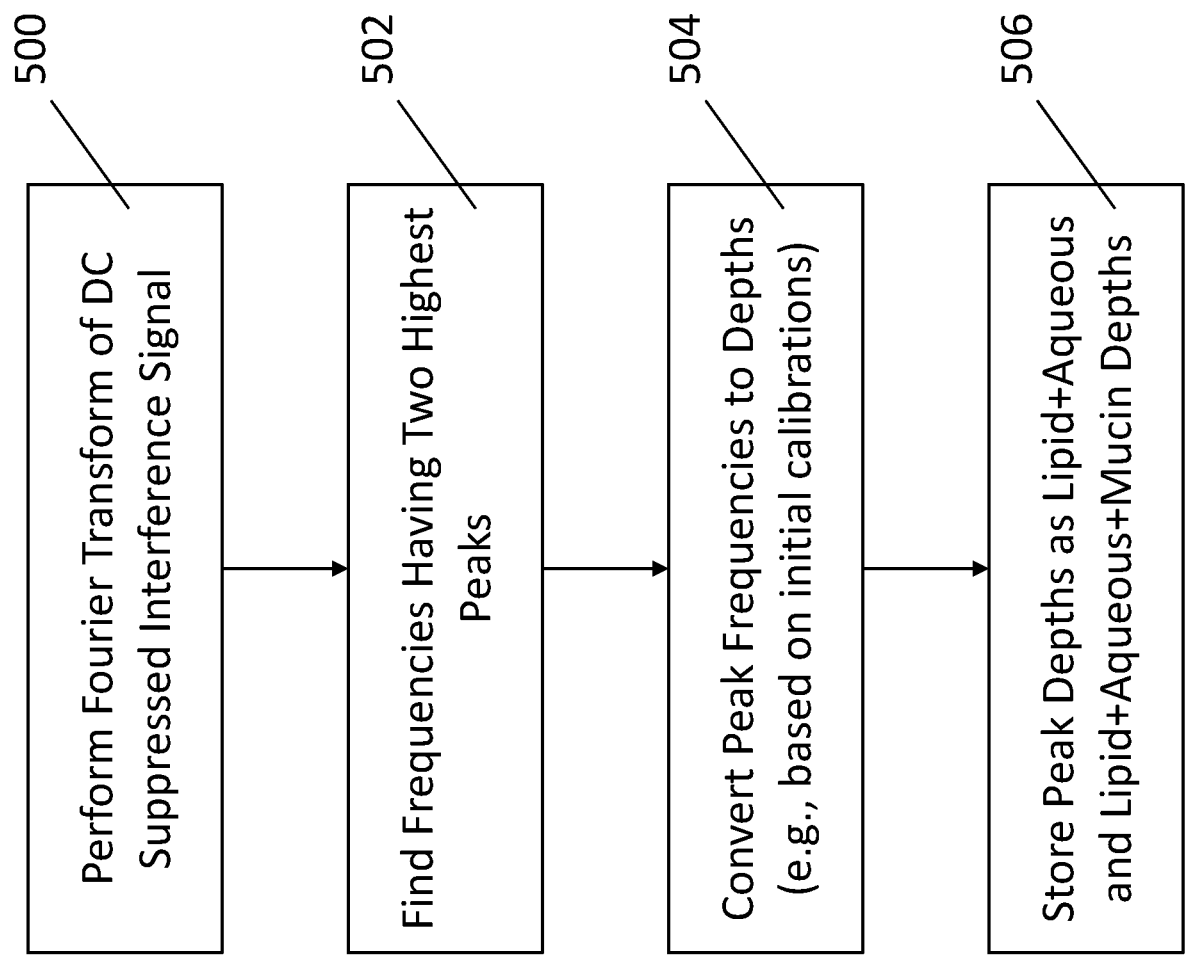
FIG. 5 illustrates an example method of the present disclosure determining combined lipid and aqueous, and lipid, aqueous, and mucin layer depths.

Referring back to FIG. 3, depths corresponding to OpticalInterference #2 (L+A) and OpticalInterference #3 (L+A+M) are identified 304 in parallel with OpticalInterference #1 and the lipid layer thickness. Th process for determining OpticalInterference #2 and OpticalInterference #3 is similar to that above for OpticalInterference #1, but without the harmonic frequency modulation. An example of such a process is shown in FIG. 5. Therein, a Fourier transform is performed directly on the interference signal (e.g., having its DC term suppressed) 500. The frequencies having the two highest peaks (the greatest frequency components in the interference signal) are then identified (e.g., by peak detection methods) 502, and those frequencies converted to depths (e.g., based on an initial calibration or similar technique as described above) 504. Similar to above, other embodiments may convert the entire signal to depth prior to identifying the largest peaks. The depth at the greatest component frequency (having the highest peak) corresponds to the depth of OpticalInterference #2 (the depth of the lipid and aqueous layers together; the depth of the aqueous mucin layer interface), and the depth at the second greatest component frequency corresponds to the depth of OpticalInterference #3 (the depth of the lipid, aqueous, and mucin layers together). It is noted that in some instances the second peak signal from the mucin layer may not be visible due to low optical reflectivity, in general. A depth profile 604 as measured by the harmonic frequency modulation method described above is illustrated in FIG. 6, with the greatest peak corresponding to OpticalInterference #2 being at 990.2 nm. However, the depth of the mucin layer may still be determined based on the depths of the aqueous and lipid layers by considering the above-noted relationship between the depths and the interference signals (and as also discussed below). These depths can then be stored 506 for later analysis.

Referring back to FIG. 3, with the depths corresponding to OpticalInterference #1, OpticalInterference #2, and OpticalInterference #3 all known (e.g., as stored from the methods of FIGS. 4 and 5), the individual depths for each layer can be solved for. Based on the above equations for each optical interference:

Lipid layer thickness (L)=OpticalInterference #1 (as stored from the process of FIG. 4);

Aqueous layer thickness (A)=OpticalInterference #2 (as stored from the process of FIG. 4) minus OpticalInterference #1 (the lipid layer thickness, stored from the process of FIG. 4); and Mucin layer thickness (M)=OpticalInterference #3 (as stored from the process of FIG. 5) minus OpticalInterference #2 (as stored from the process of FIG. 4).

In other words, the aqueous layer and the mucin layer thicknesses can be calculated by subtracting the lipid layer thickness from lipid plus aqueous and/or lipid plus aqueous plus mucin layer thickness(es) determined from OpticalInterference #2 and OpticalInterference #3. Using the example of FIG. 6, the lipid layer thickness (L) (OpticalInterference #1) is 48.525 nm, which is the depth of the greatest peak of the lipid layer depth profile 606. The aqueous layer thickness (A) is thus the difference between the depth corresponding to aqueous plus the lipid layer thickness (OpticalInterference #2) and OpticalInterference #1. That is, the aqueous layer thickness is equal to 990.2 nm-48.525 nm=941.675 nm. In this example, the input interference signal was modulated three times, and amplified by a fixed scale factor after each modulation to preserve the original signal-to-noise ratio.

While the above processes corresponding to FIGS. 4 and 5 are described as performed in parallel, it is noted that they need not be performed simultaneously. Rather, the determination of OpticalInterference #1 (the lipid layer thickness) is simply determined separately from OpticalInterference #2 and OpticalInterference #3 (the collective thicknesses of the lipid, and aqueous layers; and the lipid, aqueous, and mucin layers). In this manner, the process of FIG. 4 may be performed before or after that of FIG. 5, but both are completed after loading/obtaining and preprocessing the interference signal, and prior art finally solving for the aqueous and mucin layer thicknesses.

Finally, after each layer thickness is calculated, the final results may be displayed and/or saved for later use, and any additional information from the interference signal may be extracted for analysis, storage, display, or the like 308. Such additional information may include the optical phase of optical interference signal, or fluid properties such as viscosity, flow velocity, and/or medium deformations, vibrations, and/or changes.

More particularly, the harmonic modulated signal (e.g., as derived according to the method of FIG. 4 when determining lipid layer thickness) may still carry optical phase (0) information of the original interference signal. This optical phase information can be useful for estimating and analyzing optical and fluid properties of the tear film, such as viscosity, particle movement, temperature, refractive index, and the like. The optical phase information can be extracted by taking the Fourier transform of the modulated interference signal. In general, knowledge of the optical phase.

In general, the optical interferometry signal, $I(x, v, t)$, can be written as:

$$I(x,v,t)=2\cdot S(v)\cdot\int\sqrt{R(x,v,t)}\cos(2\pi v\tau+\Phi_0)d\tau \approx \cos(2\pi v\tau+\Phi_0)$$

where $v$ is the detected light frequency; the range information is given by the propagation time $\tau$ of the light backscattered by the imaged sample, $R(x, \tau, t)$ is the normalized backscattering intensity at $(x, \tau)$, and $S(v)$ is the spectral density of the light source. When modulated by, for example a cosine signal then, the modulated interferometry signal after attenuation compensation corresponds to:

$$I(X,v,t)_{modulated} \approx \cos[2\times(2\pi v\tau+\Phi_0)]$$

as discussed above with respect to trigonometric identities. Performing a Fourier transformation towards $v$ on an interference signal retrieves the depth information about the sample. The Fourier transformation can be written as:

$$I(x,z,t)=FT[I(x,v,t)] \approx \pi \times [\delta(z-\tau)e^{-i\Phi(x,z,t)} + \delta(z+\tau)e^{i\Phi(x,z,t)}]$$

where the optical phase term $\Phi(x, z, t)$ is generally random but fixed for static scatters of the sample at position $(x, z)$.

However, a translation of the scatter by an instantaneous distance $\Delta d(x, z)$ during a time interval $\Delta t$ between two successive B-scans induces a localized change in the measured optical phase of the reflected light given by $\Phi(x, z, t)=4\pi n\Delta d(x, z, t)/\lambda_0$ where $\lambda_0$ is the central wavelength of the light source and n is the refractive index of the sample. The measured $\Phi(x, z, t)$ is wrapped within $(-\pi, \pi)$ radians. The actual optical phase changes can thus be determined through the use of phase-unwrapping methods and the localized tear film velocity in the beam direction can be deduced from $v(x, z, t)=\Delta\Phi(x,z,t)\lambda_0(4\pi n\Delta t)^{-1}$. Sample properties such as strain rate, viscosity, etc. can then be calculated using the depth-resolved instantaneous displacement and velocity.

Figure 7:
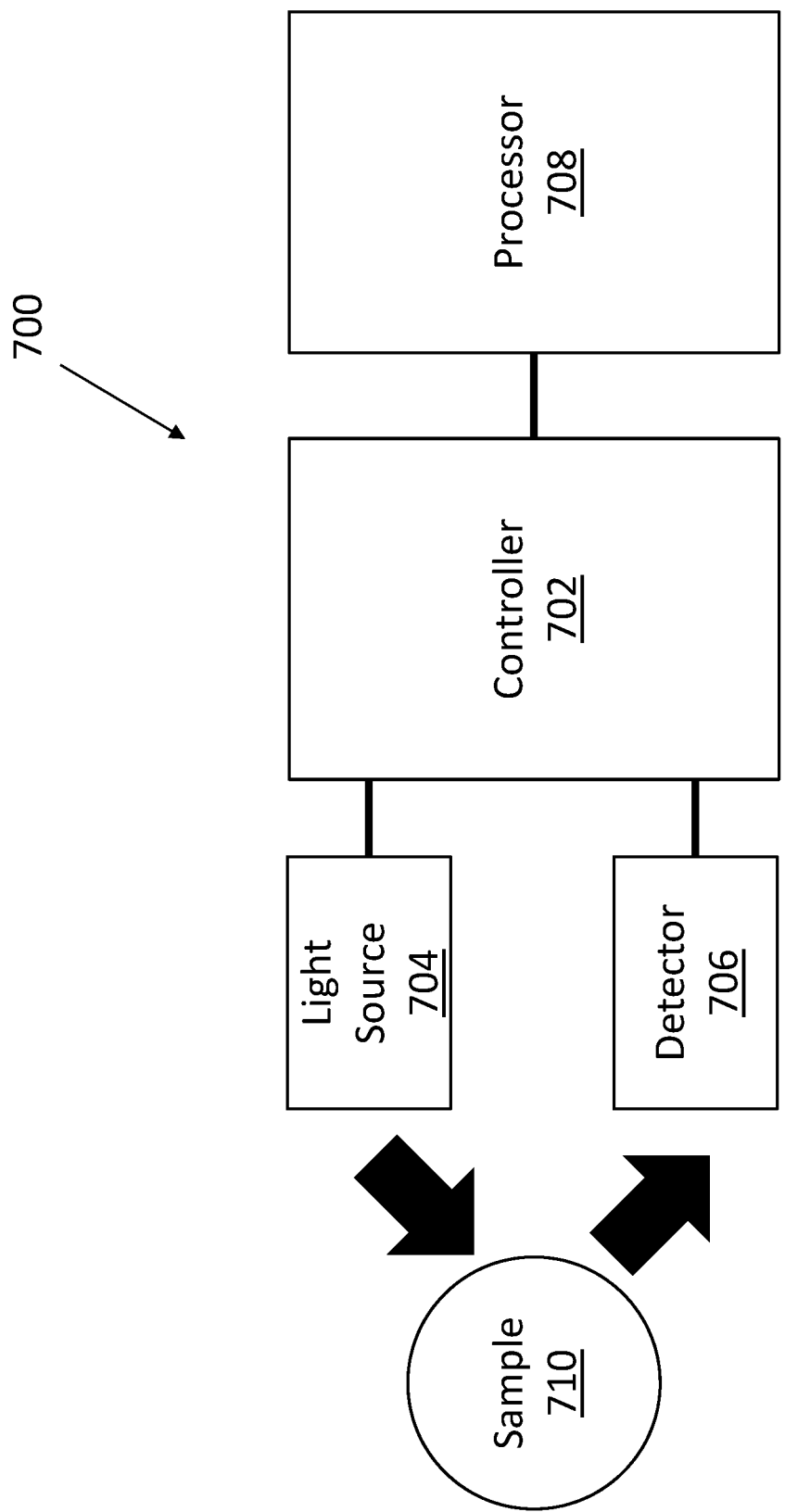
FIG. 7 illustrates an example harmonic frequency modulation system (HFMS) for carrying out the methods of the present disclosure.

It is still further noted that the above described method may be carried out on a system such as a harmonic frequency modulation system (HFMS) 700 shown in FIG. 7. In this illustration, a controller 702 is configured to control adjacent devices including a light source 704 and a detector 706. Additionally, the controller 702 communicates with a processor 708 that executes the above-described method by performing the appropriate signal processing, calculations, and the like, and controlling a display of the determined properties, such as the tear film thickness measurements, as determined according using harmonic frequency modulation method. Together, the controller 702 and processor 708 may constitute a computer (e.g., further including memory, storage devices (e.g., flash storage, hard disk drives), input/output human interface devices (e.g., keyboards, mice, touch screens, displays), and the like).

The interference signals described herein may be obtained via an interferometric imaging technique/system of a sample 710 (e.g., a subject's eye), such as low coherence interferometry (LCI), optical coherence tomography (OCT), or the like via the light source 704 and detector 706. In some embodiments the detector 706 may be a spectrometer, hyper-spectral detector/imager, or the like. In the case of tear film thickness measurements, the interference signals may be obtained by performing an LCI or OCT scan on a subject's eye during, for example, an ophthalmological screening.

The processor 708 and controller 702 may be integrated with the LCI or OCT system (e.g., sharing a common computer and peripheral devices) or may be separate (e.g., remotely located). Regardless of the integration, the described method may be performed immediately (or soon) after performing the interferometric imaging scan, or at a substantially later time; and may be performed at a clinician's office (e.g., by a clinician performing an OCT scan) or at a centralized location.

It is also noted that various signal processing may be implemented as hardware (e.g., as discrete circuitry) or as software programmed on the processor or controller. For example, a harmonic modulator circuit may be embodied as a bridge rectifier having diodes oriented clockwise or counterclockwise.

Considering the above, the methods and system described herein improve existing tear film imaging and analysis technologies by at least: 1) providing thickness measurement for each tear film; 2) measuring very thin layers, even those much thinner than the central wavelength of the light source; 3) being easier to implement; 4) measuring not only layer thickness, but also the optical phase of an optical interference signal; and 5) assessing the optical and fluid properties such as viscosity, flow velocity, medium deformation/vibration/change, etc.

While the above description relates to tear film thickness measurements, the present disclosure relates to measurement of any layer thicknesses, and in particular, for multilayer structures that include a layer too thin for its thickness to be accurately and reliably resolved. It is also noted that such multilayer structures are not limited to three layers, but could be only two layers or in other embodiments more than three layers.

What is claimed is:

1. An interferometric method comprising:
   obtaining an interference signal from an object having a first layer and a second layer, the interference signal being generated by an interferometric imaging system;
   after obtaining the interference signal:
      determining a first interference signal component of the interference signal that corresponds to a depth of the first layer; and
      determining a second interference signal component of the interference signal that corresponds to a depth of the second layer; and
   after determining the first interference signal component:
      determining a thickness of the first layer based on the first interference signal component; and
      determining a thickness of the second layer based on the thickness of the first layer and the second interference signal component,
   wherein determining the first interference signal component comprises:
      computing an envelope of the interference signal;
      iteratively applying a harmonic frequency modulation to the envelope a predetermined number of times, thereby generating a time domain modulated signal, and
   wherein the object is a tear film of the eye.

2. The method of claim 1, wherein the object further has a third layer, the second layer being between the first and third layers, the method further comprising:
   after obtaining the interference signal:
      determining a third interference signal component of the interference signal that corresponds to a depth of the third layer; and
   after determining the first, second, and third interference signal components:
      determining a thickness of the third layer based on the second interference signal component and the third interference signal component.

3. The method of claim 1, wherein determining the first interference signal component further comprises:
   performing a Fourier transform of the time domain modulated signal, thereby generating a frequency domain modulated signal; and
   identifying a frequency of the frequency domain modulated signal having a greatest intensity, and then converting the identified frequency to a depth, the depth corresponding to the depth of the first layer, or converting the frequency domain modulated signal to a depth profile, and then identifying a depth of the depth profile having a greatest intensity, the depth having the greatest intensity corresponding to the depth of the first layer.

4. The method of claim 3, further comprising:
   compensating the time domain modulated signal for attenuation caused by the harmonic frequency modulation.

5. The method of claim 3, wherein the thickness of the first layer is equal to the depth of the first layer.

6. The method of claim 3, further comprising: analyzing or estimating optical and/or fluid properties of the object based on the time domain modulated signal and/or the frequency domain modulated signal.

7. The method of claim 1, wherein determining the second interference signal component comprises:
- performing a Fourier transform of the interference signal, thereby generating a frequency domain interference signal; and
- identifying a frequency of the frequency domain interference signal having a greatest intensity, and then converting the identified frequency to a depth, the depth corresponding to the depth of the second layer, or
- converting the frequency domain interference signal to a depth profile, and then identifying a depth of the depth profile having a greatest intensity, the depth having the greatest intensity corresponding to the depth of the second layer.

8. The method of claim 7, wherein the thickness of the second layer is equal to the difference between the depth of the first layer and the depth of the second layer.

9. The method of claim 1, further comprising: preprocessing the interference signal prior to determining the first and second interference signal components.

10. The method of claim 9, wherein the preprocessing comprises suppressing a DC term of the interference signal.

11. The method of claim 1, wherein the first layer is a lipid layer, and the second layer is an aqueous layer or a mucin layer.

12. The method of claim 1, wherein the first layer is too thin to be resolved by a Fourier transform of the interference signal or of the interference signal having a DC term suppressed.

13. The method of claim 1, wherein the interference signal is acquired by a spectrometer of the interferometric imaging system.

14. A method of determining a thickness of an object comprising:
- obtaining an interference signal from the object;
- computing an envelope of the interference signal;
- iteratively applying a harmonic frequency modulation to the envelope a predetermined number of times, thereby generating a time domain modulated signal;
- performing a Fourier transform of the modulated signal, thereby generating a frequency domain modulated signal; and
- identifying a frequency of the frequency domain modulated signal having a greatest intensity, and then converting the identified frequency to a depth, the depth corresponding to the thickness of the object, or
- converting the frequency domain modulated signal to a depth profile, and then identifying a depth of the depth profile having a greatest intensity, the depth having the greatest intensity corresponding to the thickness of the object,
- wherein the object is a tear film of the eye.

15. The method of claim 14, further comprising: compensating the time domain modulated signal for attenuation caused by the harmonic frequency modulation.

16. The method of claim 14, further comprising: preprocessing the interference signal prior to computing the envelope of the interference signal.

17. The method of claim 16, wherein the preprocessing comprises suppressing a DC term of the interference signal.

18. The method of claim 14, wherein the thickness is of a lipid layer of the tear film.

19. The method of claim 14, wherein the first layer is too thin to be resolved by a Fourier transform of the interference signal or of the interference signal having a DC term suppressed.

20. The method of claim 14, further comprising: analyzing or estimating optical and/or fluid properties of the object based on the time domain modulated signal and/or the frequency domain modulated signal.

21. The method of claim 14, wherein the interference signal is acquired by a spectrometer.

* * * * *